United States Patent
Tranvouez-Bernardin et al.

(10) Patent No.: US 12,386,199 B2
(45) Date of Patent: Aug. 12, 2025

(54) METHOD FOR DETERMINING A PROGRESSIVE LENS AND ASSOCIATED SYSTEM

(71) Applicants: Essilor International, Charenton-le-pont (FR); UNIVERSITE DE MONTREAL, Montreal (CA)

(72) Inventors: Delphine Tranvouez-Bernardin, Saint Laurent (CA); Jocelyn Faubert, Montreal (CA); Guillaume Giraudet, Charenton-le-pont (FR)

(73) Assignees: Essilor International, Charenton-le-Pont (FR); UNIVERSITE DE MONTREAL, Montreal (CA)

( * ) Notice: Subject to any disclaimer, the term of this patent is extended or adjusted under 35 U.S.C. 154(b) by 669 days.

(21) Appl. No.: 17/298,388

(22) PCT Filed: Nov. 27, 2019

(86) PCT No.: PCT/EP2019/082814
§ 371 (c)(1),
(2) Date: May 28, 2021

(87) PCT Pub. No.: WO2020/109431
PCT Pub. Date: Jun. 4, 2020

(65) Prior Publication Data
US 2022/0121040 A1  Apr. 21, 2022

(30) Foreign Application Priority Data
Nov. 30, 2018 (EP) .................................... 18306597

(51) Int. Cl.
*G02C 7/02* (2006.01)
*G02C 7/06* (2006.01)

(52) U.S. Cl.
CPC ............. *G02C 7/027* (2013.01); *G02C 7/028* (2013.01); *G02C 7/068* (2013.01)

(58) Field of Classification Search
CPC ........ G02C 7/027; G02C 7/028; G02C 7/068; A61B 3/0025; A61B 5/103; A61B 5/6821
USPC ....... 351/159, 228, 246, 241, 223, 219, 216, 351/209, 203, 243, 247
See application file for complete search history.

(56) References Cited

U.S. PATENT DOCUMENTS

| | | |
|---|---|---|
| 5,861,935 A | 1/1999 | Morris et al. |
| 6,074,062 A | 6/2000 | Morris et al. |

(Continued)

FOREIGN PATENT DOCUMENTS

WO  WO-2016020229 A1 *  2/2016  ............. G02C 7/027

OTHER PUBLICATIONS

Guilino et al., "Progressiv R: The new progressive lens from Rodenstock", Mar. 13, 1982, The Ophthalmic Optician, pp. 1-4 (Year: 1982).*

(Continued)

*Primary Examiner* — Wyatt A Stoffa
*Assistant Examiner* — Samanvitha Sridhar
(74) *Attorney, Agent, or Firm* — Oblon, McClelland, Maier & Neustadt, L.L.P.

(57) ABSTRACT

A method for determining a design of a progressive lens intended to be worn by a future wearer, the progressive lens comprising a front surface and a back surface, at least one of the front surface and the back surface comprising a progression profile on its general spherical shape, said at least one progression profile defining a meridian line extending from a distance-vision point to a near-vision point, said meridian line comprising a vertical portion passing through the distance-vision point and an inclined portion passing through the near-vision point, the vertical portion and the inclined portion forming an angle between them, the method (Continued)

including obtaining first data representative of a first measurement of a first postural instability of the future wearer when seeing a visual pattern moving along an mediolateral direction, and determining a reparation between the first progression profile and the second progression profile based on the first data.

16 Claims, 5 Drawing Sheets

(56) References Cited

U.S. PATENT DOCUMENTS

| | | |
|---|---|---|
| 2010/0271590 A1 | 10/2010 | Kitani et al. |
| 2012/0019776 A1* | 1/2012 | Giraudet .............. G02C 7/027 |
| | | 351/159.75 |
| 2012/0092614 A1 | 4/2012 | Drobe et al. |
| 2015/0230732 A1 | 8/2015 | Faubert et al. |
| 2017/0090220 A1 | 3/2017 | Bonnin et al. |
| 2022/0026741 A1* | 1/2022 | Tranvouez-Bernardin .................. |
| | | G02C 7/027 |

OTHER PUBLICATIONS

International Search Report and Written Opinion issued Mar. 10, 2020 in PCT/EP2019/082814 filed Nov. 27, 2019.
Extended European Search Report issued Feb. 19, 2019 in European Patent Application No. 18306597, filed Nov. 30, 2018.

* cited by examiner

METHOD FOR DETERMINING A PROGRESSIVE LENS AND ASSOCIATED SYSTEM

FIELD OF THE DISCLOSURE

The present disclosure relates to a method for determining a progressive addition lens and associated system.

BACKGROUND OF THE DISCLOSURE

An ophthalmic progressive addition lens, or PAL, has an optical power that varies progressively along a line over the surface of this lens, known as meridian line. The meridian line connects a distance-vision point on the lens, to which the optical power and astigmatism of the lens are adapted in order to correct the distance vision of a wearer, to a near-vision point to which the optical power is adapted in order to correct the near vision of the wearer. PALs are designed to correct the ametropia and presbyopia of the wearer in the near-vision and distance-vision zones but also to provide comfortable vision at all distances between the near-vision zone and the distance-vision zone on the meridian line. Aberrations remain in the peripheral areas on both sides of the meridian line between the distance-vision zone and the near-vision zone. To limit the impact of these aberrations, PALs are designed to optimally respect all physiological visual functions, in particular:

- foveal vision where coordination of the body, head and eye movements, in relation to the objects' location in the vision, defines the power value needed at each point of the progression. The field of gaze is determined by the natural coordination of horizontal eye and head movements;
- extra-foveal vision (provided by the periphery of the retina) which provides space and form perception and is directly influenced by the distribution of prism on the progressive lens surface. The variation of prismatic effects plays also a role in the wearer's comfort when movement is perceived;
- binocular vision where, for optimal fusion of the simultaneous perception of the two eyes, the images produced by the right and left lenses must be formed on corresponding retinal points and display similar optical properties in all directions of gaze.

Progressive lens designers work towards respecting these physiological functions and propose a limited number of optimized designs which are tested through rigorous clinical trials.

The optometrist or ophthalmologist proposes usually a lens "model design" that may be the result of an analysis of the viewing behavior of the wearer and/or the type of activities intended to be performed, for example. Each "model design" corresponds to a design optimized for different design features and constraints. For example, the different design features may be selected in the list consisting of size parameters of the different vision zones of the progressive addition lens (such as for example the near vision zone, the intermediate vision zone, the distance vision zone), inset, frame design parameters, viewing preferences. The actual design of the progressive lens to be manufactured is then calculated using a particular "model design" and by determining the surface characteristics of the lens to be manufactured as a function of the prescription of the wearer.

It has been observed that, due to the presence of aberrations in the peripheral region, some designs of progressive lenses induce more vertigo and motion sickness, i.e. postural instability, while others don't.

It has also been observed that some wearers are more or less subject to postural instability when they are exposed to a visual pattern moving in their field of view in the peripheral area for example.

There is thus a need to determine a progressive lens that reduces the vertigo and motion sickness of a future wearer.

PRESENTATION OF THE DISCLOSURE

One aim of the disclosure is to provide a design of a progressive lens intended to be worn by a future wearer that reduces the postural instabilities induced by the progressive lens.

To this end, it is proposed, according to a first aspect, a method for determining a design of a progressive lens intended to be worn by a future wearer, the progressive lens comprising a front surface and a back surface, the front surface comprising a first progression profile and the back surface comprising a second progression profile, said first and second progression profiles, the method comprising:

- obtaining first data representative of a first measurement of a first postural instability of the future wearer when seeing a visual pattern moving along a mediolateral direction,
- determining, by at least a processor, a repartition between the first progression profile and the second progression profile based on the first data.

According to an embodiment, when said repartition is defined by a progression profile on the back surface versus a complementary progression profile on the front surface, said repartition is an increasing function of said first postural instability.

According to an embodiment, said first and second progression profiles defining a meridian line extending from a distance-vision point to a near-vision point, said meridian line comprising a vertical portion passing through the distance-vision point and an inclined portion passing through the near-vision point, the vertical portion and the inclined portion forming an angle between them, the method further comprising:

- obtaining second data representative of a second measurement of a second postural instability of the future wearer when seeing a visual pattern moving along an anterior-posterior direction,
- determining, by said at least one processor, the angle of the inclined portion based on said second data.

According to an embodiment, the method further comprises;

- obtaining a comparison value representing a comparison between the first measurement and the second measurement, said comparison value being increased when the first measurement increases while the second measurement decreases, and being decreased when the first measurement decreases while the second measurement increases,
- when said comparison value is lower than a first threshold, then the second progression profile is set to correspond to the full progression profile of the ophthalmic lens, while the first progression profile is set to be null, and when said comparison value is greater than the first threshold, the first progression profile is set to increase as the comparison value increases while the second progression profile decreases,
- when said comparison value is greater than a second threshold, the angle of the inclined portion is equal to 180°, while when said comparison value is less than the second threshold, the angle of the inclined portion decreases as the comparison value decreases, the second threshold being greater than the first threshold.

In particular execution modes, the comparison value is determined by the processor(s) and/or is a computed value.

In alternative modes, the comparison value is received by the processor(s).

In other particular modes, the comparison value is directly derived from the first and second measurements, such as by means of a look-up table. Such a table may e.g. be based on dedicated respective ranges for the first measurement and the second measurement as table inputs, and the comparison value as a table output.

According to an embodiment, when said comparison value is greater than a third threshold lower than said second threshold, the angle of the inclined portion continuously increases from a prescribed angle value to 180°.

According to an embodiment, when said comparison value is between said first threshold and a fourth threshold greater than said first threshold, the second progression profile continuously decreases from the first threshold to reach a null progression profile at said fourth threshold, while the first progression profile continuously increases to reach the full progression profile at said fourth threshold.

According to an embodiment, the fourth threshold is lower than the third threshold.

It is also proposed, according to a second aspect, a system for determining a design of a progressive lens intended to be worn by a future wearer, the progressive lens comprising a front surface and a back surface, the front surface comprising a first progression profile and the back surface comprising a second progression profile, wherein the system comprises:

at least one processor configured for:
    obtaining first data representative of a first measurement of a first postural instability of the future wearer when seeing a visual pattern moving along a mediolateral direction,
    determining a repartition between the first progression profile and the second progression profile based on said first data.

According to particular implementations, said first and second progression profiles define a meridian line extending from a distance-vision point to a near-vision point, said meridian line comprising a vertical portion passing through the distance-vision point and an inclined portion passing through the near-vision point, the vertical portion and the inclined portion forming an angle between them, said at least one processor being further configured for:

obtaining second data representative of a second measurement of a second postural instability of the future wearer when seeing a visual pattern moving along an anterior-posterior direction, determining the angle (a) of the inclined portion based on said second data.

According to a more specific embodiment, the at least one processor is further configured for:

obtaining a comparison value representing a comparison between the first measurement and the second measurement, said comparison value being increased when the first measurement increases while the second measurement decreases, and being decreased when the first measurement decreases while the second measurement increases, when said comparison value is lower than a first threshold, then the second progression profile is set to correspond to the full progression profile of the ophthalmic lens, while the first progression profile is set to be null, and when said comparison value is greater than the first threshold, the first progression profile is set to increase as the comparison value increases while the second progression profile decreases, when said comparison value is greater than a second threshold, the angle of the inclined portion is equal to 180°, while when said comparison value is less than the second threshold, the angle of the inclined portion decreases as the comparison value decreases, the second threshold being greater than the first threshold.

According to an embodiment, the system further comprises:

a device configured to:
    display a visual pattern moving at least along at least an anterior-posterior direction,
    measure the postural instability of the future wearer when the future wearer is seeing a visual pattern along at least an anterior-posterior direction.

It is also proposed, according to a third aspect, a computer program product comprising a series of instructions that, when they are executed by a processor, implements the method previously described.

It is also proposed, according to a fourth aspect, a non-transitory computer-readable storage medium, storing the computer program previously described.

According to the disclosure, a design of progressive lens which takes into account the sensitivity of a future wearer to motion in a mediolateral direction is proposed in order to control the postural instability of the wearer induced by the progressive lens. Further, the inventors have discovered that some wearers are also sensitive to motion in an anterior-posterior direction. Thus, the sensitivity of the future wearer to motion in the anterior-posterior direction is also taken into account to determine the design of the progressive lens. The sensitivity of the future wearer to motion in a particular direction is quantified by measuring the postural instability of the wearer when the wearer is seeing a displayed visual pattern moving in that particular direction and a design parameter is determined as a function of these measurements. According to an embodiment, the amount of progression distributed between the front surface and the back surface of the progressive lens may be determined as a function of the postural instability measured when the wearer is seeing a visual pattern moving in a mediolateral direction and the angle of the inclined portion of the meridian line is determined as a function of the postural instability measured when the wearer is seeing a visual pattern moving in an anterior-posterior direction. According to another embodiment, the design of the progressive lens is determined depending on which of the sensitivity of the future wearer to motion in the anterior-posterior direction or the sensitivity of the future wearer to motion in the mediolateral direction prevails.

BRIEF DESCRIPTION OF THE DRAWINGS

Further details, aspects and embodiments of the proposed solution will be described, by way of example only, with reference to the drawings.

DESCRIPTION

In the framework of the disclosure, the following terms have the meanings indicated herein below:
- optical axis of the addition lens: direction perpendicular to the front surface of the lens and passing through the optical centre of the latter;
- distance-vision zone: region of the lens that surrounds the distance-vision point, and within which the local optical characteristics of optical power and of astigmatism of the lens are substantially identical to those at the distance-vision point;
- near-vision zone: region of the lens that surrounds the near-vision point, and within which the local optical characteristics of optical power and of astigmatism of the lens are substantially identical to those at the near-vision point;
- addition of a progressive lens: difference between the value of optical power of the lens at the near-vision point and that at the distance-vision point;
- optical characteristics of a lens: data on optical power, astigmatism, relating to the modifications of a light beam that passes through the lens;
- prescription: set of optical characteristics of optical power, of astigmatism and, where relevant, of addition, determined by an ophthalmologist in order to correct the vision defects of an individual, for example by means of a lens positioned in front of his eye. The term 'astigmatism' is used to denote the data pair formed by an amplitude value and a value of angle. Although this is an abuse of language, it is also sometimes used to denote the amplitude of the astigmatism only. The context allows those skilled in the art to understand which usage of the term is intended. Generally speaking, the prescription for a progressive lens comprises values of optical power and of astigmatism at the distance-vision point and, where appropriate, an addition value;
- surface characteristics of a lens: geometrical data relating to one surface of the lens, such as values of average sphere or cylinder, for example;
- average sphere, denoted D: (N−1) times the half-sum of the inverses of the two radii of curvature of a surface, denoted R1 and R2, and determined at the same point on the latter. In other words: D=(N−1)×(1/R1+1/R2), where N is the index of refraction of the lens, and
- cylinder, denoted C: (N−1) times the absolute value of the half-difference of the inverses of the two radii of curvature of a surface, determined at the same point on the latter. In other words: C=(N−1)×(1/R1−1/R2).

Figure 1A:
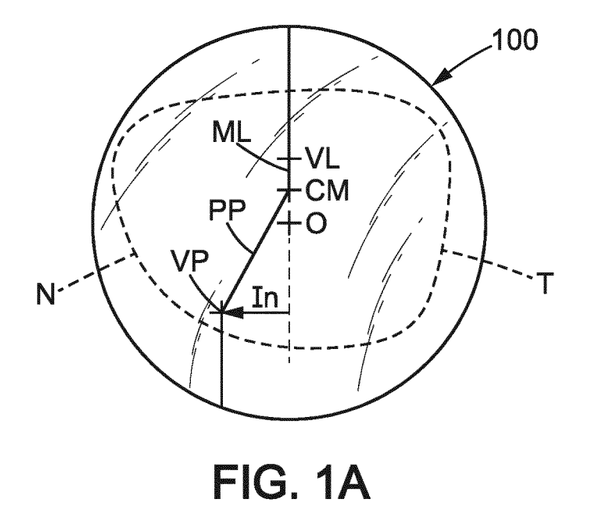
FIGS. 1A and 1B are schematic plan and cross-sectional views, respectively, of an ophthalmic progressive addition lens, which indicates certain geometrical or optical data on this lens.

FIG. 1A shows schematically a progressive addition lens 100 before the latter has been cut out around a contour C to the dimensions of a frame recess of a pair of glasses. The point O corresponds to the optical center of the lens and the point CM corresponds to the mounting cross. The nasal and temporal sides of the lens, respectively denoted N and T are also represented.

The progressive addition lens 100 comprises at least a progression profile PP extending from a distance-vision point VL to a near-vision point VP and defining a meridian line ML.

The progression profile PP defines a variation of optical power along the meridian line ML. On the meridian line ML, the optical power varies continuously between the distance-vision point VL and the near-vision point VP between a prescription value for far-distance vision to a value for near-distance vision corresponding to the prescribed optical power for distance-vision to which is added the prescribed value of addition. The progression thus varies from 0 to the prescribed addition value between the distance-vision point VL and the near-vision point VL. Usually, the progression varies only on a part of the meridian line between the near-vision zone and the distance-vision zone, i.e. in the intermediate zone, on a length defined by the progression length. It may be noted that the progression profile and in particular the progression length have an influence on the aberrations induced in the intermediate zone on both sides of the progression profile.

It may also be noted that the meridian line ML is not a straight line between the distance-vision point VL and the near-vision point VP as the eyes of the user progressively converge towards the nasal side of the lens while looking at objects in front of him which become closer to him. As schematically illustrated in FIG. 1A, the meridian line ML comprises a vertical portion passing through the distance-vision point VL and an inclined portion passing through the near-vision point VP. Usually, the vertical portion and the inclined portion form an angle α due to the convergence of the eyes of the user while looking at objects which become closer to him. The near-vision point VP is thus shifted horizontally with respect to the vertical portion passing through the distance-vision point, when the lens is in a position of use by its wearer. This shift, which is in the direction of the nasal side of the lens, is usually referred to as "inset". Usually, the near-vision point is shifted in order to take into account the fact that the eyes of the wearer converge when looking at an object in the near-vision zone, at a particular distance from the wearer. In the embodiment described here, the meridian line ML comprises a vertical portion between the distance-vision point VL and the mounting cross CM and an inclined portion between the mounting cross CM and the near-vision point VP. The angle α corresponds to the angle between the vertical portion of the meridian line and the segment joining the mounting cross CM and the near-vision point VL. On the progression profile, the average sphere is continuously varied between the distance-vision point and the near-vision point to provide a given value of addition at the near-vision point.

Figure 1B:
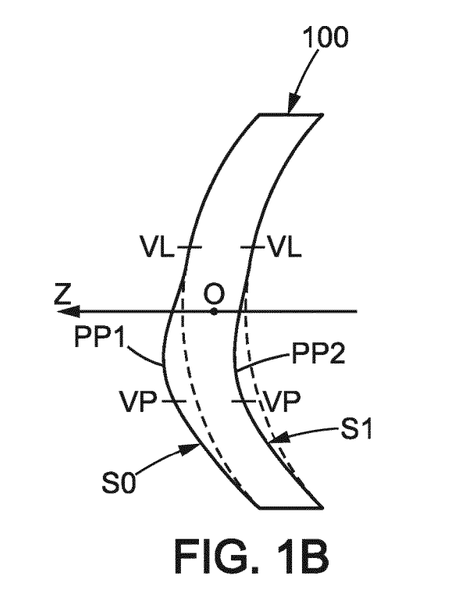

FIG. 1B represents schematically a cross-sectional view of the progressive lens 100 along the meridian line. The progressive lens comprises a front and a back surface, respectively denoted S0 and S1, together with the optical axis of the lens, denoted Z. The front and back surfaces of the lens have a general spherical shape, the front surface being convex and the back surface being concave. According to the disclosure, at least one of the front surface and back surface comprises a progression profile. Here, as may be seen in FIG. 1B, the progressive lens comprises a first progression profile PP1 on the front side S0 of the progressive lens and a second progression profile PP2 on the back surface S1 of the lens. Thus, the average sphere varies locally on both surfaces. Otherwise, the average sphere is constant on the surface of the progressive lens which has no progression profile as represented by the dotted lines. The surface without progression on its surface usually has a constant cylinder to provide the astigmatism correction for the wearer.

When the progressive lens comprises only a progression profile on one of the front surface or back surface, the progression profile then corresponds to the full progression profile, i.e. the addition at the near-vision point corresponds to the prescribed addition of the wearer. When the progressive lens 100 comprises a progression profile on the front surface and a progression profile on the back surface, the progressive lens may be referred to as a "dual" progressive lens. The full progression of the lens is then distributed on the front and on the back surface of the progressive lens.

Figure 2:
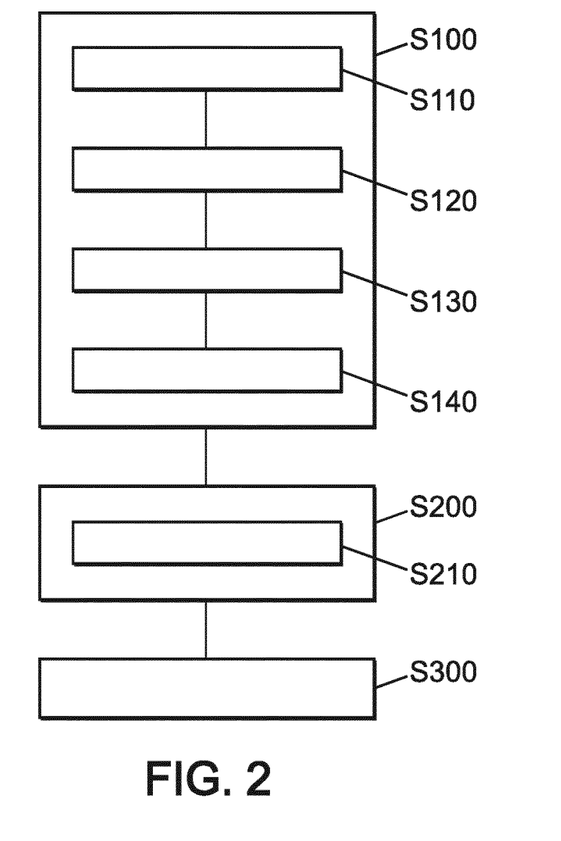
FIG. 2 illustrates a method for determining a design of a progressive lens according to a first embodiment.

FIG. 2 illustrates a method for determining a design of a progressive lens according to a first embodiment in which only the sensitivity of the wearer to motion in the mediolateral direction is taken into account. The mediolateral direction corresponds to a horizontal direction in a plane parallel to the frontal plane which is perpendicular to the median plane.

The method comprises a step S100 of obtaining a first measurement of the postural instability of the future wearer when seeing a visual pattern moving along a mediolateral direction and a step S200 of determining the design of the progressive lens based on said measurement.

The step S100 comprises a step S110 of displaying a visual pattern moving along a medio-lateral direction and a step S120 of measuring the postural instability of the future wearer while the future wearer is seeing the visual pattern. The step S100 further comprises a step S130 of displaying a reference visual pattern and a step S140 of measuring the postural instability of the future wearer while the future wearer is looking at the reference visual pattern.

The steps S110 and S130 of displaying a visual pattern are performed by a display device which may be a virtual reality headset, a display such as a LCD, plasma or OLED screen which is inclined for example, or a projector configured to project the visual pattern on an inclined surface such as a semi-transparent surface for example. An example of such a display device is described in WO 2014/040186.

The visual pattern may be a geometric, spatially periodical, high contrast pattern such as a checkerboard pattern for example. The visual pattern may move repetitively along the mediolateral direction and have a periodical back and forth motion for example. The reference pattern may correspond to a static visual pattern or to a visual pattern moving randomly in a plurality of directions.

The steps S120 and S140 of measuring the postural instability of the future wearer when the wearer is seeing a visual pattern comprise measuring changes in the body posture of the wearer induced by the viewing of the visual pattern. The changes in the body posture of the wearer may be measured by detecting movements of the future wearer.

According to an embodiment, the movements of the future wearer are measured by placing a plurality of optical targets on the wearer and by evaluating the displacement and the velocity of displacement of these optical targets using camera recordings of the future wearer. The postural instability is then measured by computing the velocity root mean square value, i.e. VRMS, of the displacement measured by the plurality of targets when the wearer is seeing a visual pattern moving along a mediolateral direction. According to an embodiment, the measurement of the postural instability of the wearer may comprise measuring the VRMS of the displacement of the targets when the future wearer is not seeing any moving pattern and by computing a ratio between the two different VRMS values. This ratio may be expressed as a percentage of increase in the postural instability of the wearer for example.

According to another embodiment, the movements of the future wearer may be measured by placing movement sensors on the wearer or by measuring changes of pressure exerted by the feet of the wearer when the future wearer is placed on a force platform.

Advantageously, the postural instability measured when the future wearer is viewing a visual pattern moving along a mediolateral direction is divided by the postural instability measured when the future wearer is viewing the reference visual pattern. This enables to normalize the postural instability of the wearer and to allow a comparison between different wearers.

The step S200 comprises a step S210 of determining a reparation of the full progression profile of the progressive lens between the first progression profile and the second progression profile as a function of the measurement of the postural instability obtained in step S100.

According to an embodiment, when the first measurement of the postural instability is less than a first predetermined value, the first progression profile is set to correspond to the full progression profile of the progressive lens while the second progression profile is set to be null, and when the measurement of the postural instability is greater than a second predetermined value, the second progression profile is set to correspond to the full progression profile while the first progression profile is set to be null.

Thus, the progressive lens thus only has a progression profile on the back surface of the lens, when the wearer is very sensitive to motion in the mediolateral direction in order to reduce the difference of magnification between the distance-vision and the near-vision regions responsible for image jump and distortions causing a postural instability of the wearer when seeing visual patterns moving in the mediolateral direction. This effect is also known as the "swim effect". To the contrary, when the wearer is not very sensitive to motion in the mediolateral direction, the full progression of the progressive lens may be placed on the front surface of the lens.

According to an embodiment, when the measurement of the postural instability is greater than the first predetermined value, the second progression profile continuously decreases from the first predetermined value to reach a null progression profile at said second predetermined value, while the first progression profile continuously increases to reach the full progression profile at said second predetermined value.

Thus, between these two values, the repartition of the full progression profile between the first and the second progression profiles may optionally be varied depending on the sensitivity of the wearer to motion in the mediolateral direction to reduce the postural instability induced by the progressive lens.

Once the repartition between the first progression profile and the second progression profile is determined, the design of the progressive lens, i.e. the surface characteristics of the lens to be manufactured, may be determined as a function of the prescription of the wearer using methods known of the person skilled in the art.

According to an embodiment, the design of the progressive lens may be obtained by running an optimization algorithm configured to maximize a merit function while taking into account different constraints and design parameters including the repartition of the full progression of the lens between the first and the second progression profiles determined in step S210.

Figure 5:
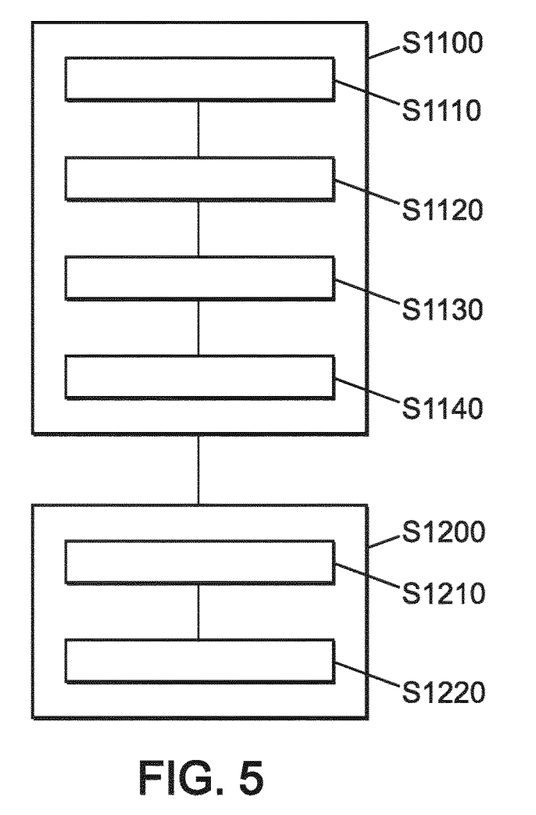
FIG. 5 represents a method for determining a design of a progressive lens according to a second embodiment.

FIG. 5 illustrates a method for determining a design of a progressive lens according to a second embodiment. In this second embodiment, the sensitivity of the wearer to motion in the mediolateral direction and in an anterior-posterior direction is taken into account. The anterior-posterior direction corresponds to any horizontal direction in a plane parallel to the median plane, which is a vertical plane that splits the body of the wearer in a right part and a left part.

The inventors have discovered that the sensitivity of wearers to motion in the anterior-posterior direction and in the mediolateral direction may be different from a wearer to another and thus propose to determine the design of the progressive lens accordingly.

The inventors have discovered that increasing the angle α, and thus reducing the inset, contributes to reduce the postural instability perceived by a wearer of progressive lenses when seeing a visual pattern moving in the anterior-posterior direction.

Figure 3A:
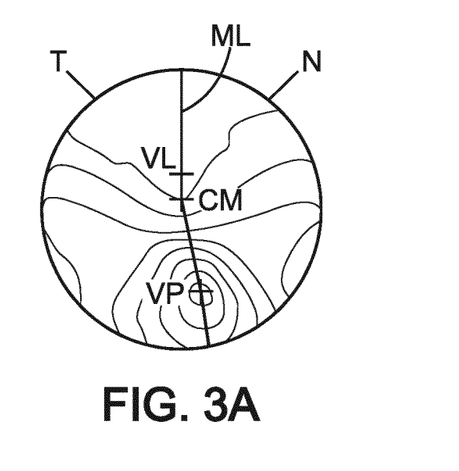
FIGS. 3A and 3B show, respectively, isocurves of the spherical power and the cylindrical power of a progressive lens having an inset with a predetermined value intended to be placed before a left eye of a wearer.
Figure 3B:
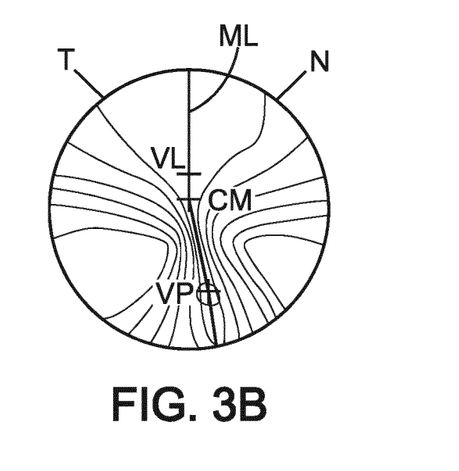
Figure 3C:
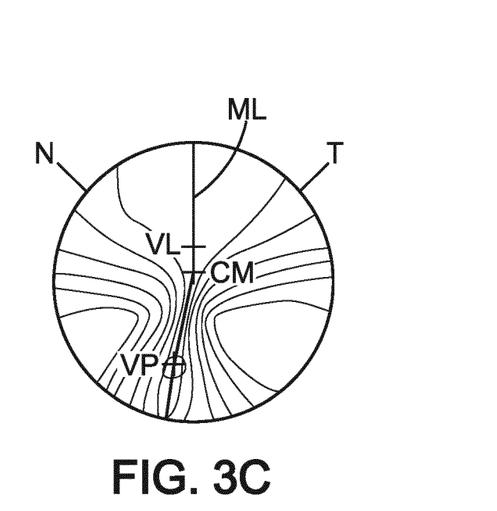
FIGS. 3C and 3D show, respectively, isocurves of the cylindrical power and the spherical power of a corresponding progressive lens having an inset with a predetermined value intended to be placed in front of a right eye of a wearer.
Figure 3D:
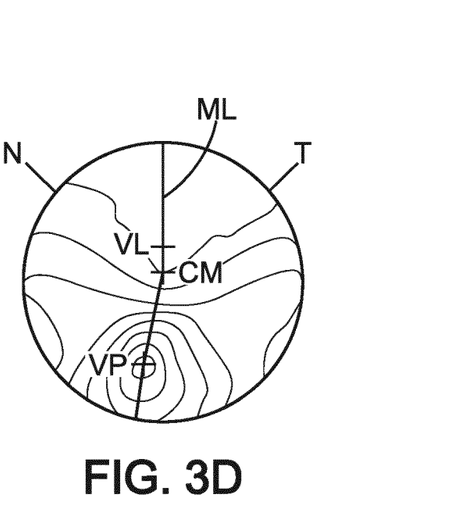
Figure 4A:
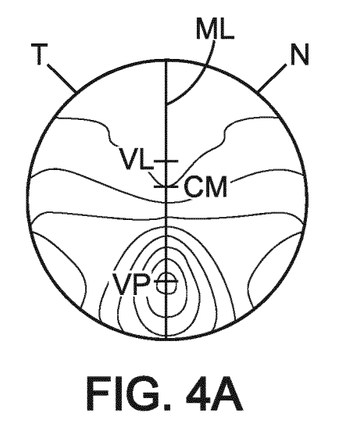
FIGS. 4A, 4B show, respectively, isocurves of the spherical power and the cylindrical power of the progressive lens of FIGS. 3A and 3B with an inset that is null intended to be placed in front of a left eye of a wearer.
Figure 4B:
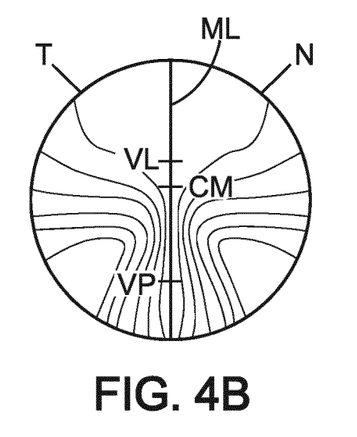
Figure 4C:
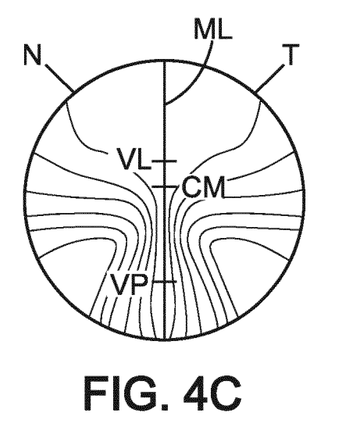
FIGS. 4C, 4D show, respectively, isocurves of the cylindrical power and the spherical power of the progressive lens of FIGS. 3C and 3D with an inset that is null intended to be placed in front of a right eye of a wearer.
Figure 4D:
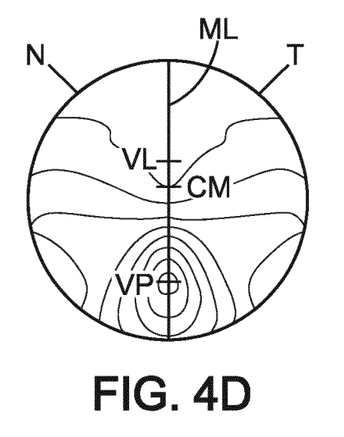

FIGS. 3A and 3B represent isocurves of average sphere and cylinder, respectively, of a progressive lens intended to be placed in front of the left eye of a wearer. FIGS. 3C and 3D represent the same isocurves of cylinder and average sphere, respectively, but for a progressive lens intended to be placed in front of the right eye of the wearer. The inclined portion of the meridian line forms an angle α with the vertical portion of the meridian line that is less than 180 degrees that is chosen to enable the natural convergence of the eyes of the wearer when seeing an object in the near-vision zone at a given distance. It may be seen that the isocurves are not symmetrical regarding the vertical portion of the meridian line. Thus, different aberrations will be applied to the same scene seen by the left eye and by the right eye which induces some additional binocular disparity. Thus, some points of the scene in a same plane may be seen at a different depth. This will induce some postural instability of the wearer.

To the contrary, as may be seen in FIGS. 4A, 4B, 4C, 4D which correspond to the same graphs as in FIGS. 3A, 3B, 3C, 3D but with an angle α set to 180 degrees, the isocurves of average sphere and cylinder are symmetrical with respect to the vertical portion of the meridian line. Thus, the same aberrations will be applied on the image seen by the left eye and the right eye and no additional binocular disparity is induced. All points of the scene in a same plane will be seen at the same depth determined by the value of the binocular disparity, i.e. the difference of position on the retina of the left eye and the right eye for a same point of the scene. The postural instability induced by motion in the anterior-posterior direction are then reduced.

Thus, the angle α, and thus the inset, may be varied to customize the progressive lens as a function of the sensitivity of the wearer to motion in the anterior-posterior direction.

According to this second embodiment, the method comprises a step S1100 of obtaining measurements of the postural instability of the future wearer when seeing a visual pattern moving along a mediolateral direction and along an anterior-posterior direction and a step S1200 of determining the design of the progressive lens based on said measurements.

The step S1100 comprises a step S1110 of displaying a visual pattern moving along the mediolateral direction ML, a step S1120 of measuring the postural instability of the future wearer while the future wearer is seeing the visual pattern displayed in step S1110, a step S1130 of displaying a visual pattern moving along a anterior-posterior direction AP and a step S1140 of measuring the postural instability of the future wearer while the future wearer is seeing the visual pattern displayed in step S1130.

The steps above are similar to the steps described previously in reference to FIG. 2, except for step S1020 in which the visual pattern is moving along an anterior-posterior direction instead of the mediolateral direction.

The step S1200 of determining the design of the progressive lens based on the measurements of the postural instability performed in steps S1120 and S1140, respectively, is further described below.

The step S1200 comprises a step S1210 of determining a computed value CV representing a comparison between the measurement of the postural instability of the wearer in the mediolateral direction and the measurement of the postural instability of the wearer in the anterior-posterior direction.

According to an embodiment, the computed value is calculated using the following equation:

$$CV = \frac{M_{AP}}{M_{ML}},$$

wherein $M_{AP}$ corresponds to the measurement of the postural instability of the wearer induced by a visual pattern moving in the anterior-posterior direction and $M_{ML}$ corresponds to the measurement of the postural instability of the wearer induced by a visual pattern moving in the mediolateral direction.

According to another embodiment, the computed value is calculated using the following equation:

$$CV = \frac{M_{AP} - M_{ML}}{M_{AP} + M_{ML}},$$

wherein $M_{AP}$ corresponds to the measurement of the postural instability of the wearer induced by a visual pattern moving in the anterior-posterior direction and $M_{ML}$ corresponds to the measurement of the postural instability of the wearer induced by a visual pattern moving in the mediolateral direction.

In both embodiments, the computed value CV increases when $M_{AP}$ increases while $M_{ML}$ decreases, and the computed value CV decreases when $M_{AP}$ decreases while $M_{ML}$ increases. The computed value may have other expressions which enable to compare the measurement of the postural instability in the anterior-posterior direction and in the mediolateral direction.

Thus, depending on the computed value, it may be determined, for the future wearer, a design of a progressive lens that is adapted to the relative sensitivity of the wearer to motion in the anterior-posterior direction and in the mediolateral direction.

Accordingly, step S1200 further comprises a step S1220 of determining the design of the progressive lens depending on the computed value.

According to an embodiment, step S1220 comprises an initialization step S1221 comprising:
  defining a progressive lens comprising a front surface having a first progression profile on its general spherical shape, a back surface of the lens having a second progression profile on its general spherical shape and an optical medium placed between the front and the back surfaces of the lens whose refractive index may be defined,
  defining a meridian line said meridian line comprising at least a vertical portion and an inclined portion, said vertical portion passing through the distance-vision point and said inclined portion passing through the near-vision point, said vertical and horizontal portions forming an angle between them.

Figure 6:
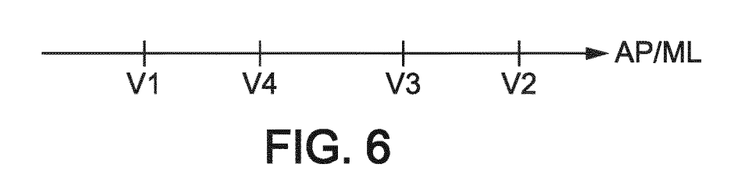
FIG. 6 illustrates different thresholds that may be used according to the second embodiment.

Step S1220 of determining the design of the progressive lens further comprises a step S1222 of comparing the computed value with at least a first and a second threshold and a step S1223 of determining the angle of the inclined portion of the meridian line and determining the repartition between the first and the second progression profiles. Different thresholds which may be used in step S1222 are represented in FIG. 6. FIG. 6 illustrates four thresholds V1, V4, V3, V2 on an axis AP/ML. AP/ML corresponds to a computed value which may be a ratio of $M_{ML}$ and $M_{AP}$ or any other expression enabling to compare the measurements of the postural instability $M_{ML}$ and $M_{AP}$. As may be seen, the first threshold V1 corresponds to a low value of AP/ML whereas the second threshold V2 corresponds to a high value of AP/ML. Further, the optional fourth threshold V4 is greater than the first threshold and the optional third threshold is less than the second threshold.

If the computed value is lower than a first threshold, then the second progression profile is set to correspond to the full progression profile of the ophthalmic lens, while the first progression profile is set to be null.

The progressive lens thus only has a progression profile on the back surface of the lens in order to reduce the difference of magnification between the distance-vision and the near-vision regions responsible for image jump and distortions causing a postural instability of the wearer when seeing visual patterns moving in the mediolateral direction. This effect is also known as the "swim effect".

If the computed value is greater than the first threshold, then the first progression profile is set to increase as the computed value increases while the second progression profile decreases. The repartition between the first progression profile and the second progression profile thus varies. The repartition may vary continuously or abruptly so that the full progression is on the front surface of the lens. Accordingly, the less the future wearer is sensible to motion in the mediolateral direction, the more progression is placed on the front surface of the progressive lens. This enables to control the "swim effect".

According to an embodiment, when the computed value is between the first threshold V1 and a fourth threshold V4, the second progression profile continuously decreases from the first threshold V1 to reach a null progression profile at said fourth threshold V4, while the first progression profile continuously increases to reach the full progression profile at said fourth threshold V4. Thus, when the computed value is comprised between the first and the fourth threshold, the full progression of the progressive lens is then distributed between the first and the second progression profiles and the amount of progression placed on the first progression profile increases. When the computed value is greater than the fourth threshold, the sensitivity of the wearer to movements in the medio-lateral direction is thus negligible and the "swim effect" is not reduced by controlling the amount of progression on the second progression profile.

Further, if said computed value is greater than a second threshold, the angle of the inclined portion is set equal to 180 degrees. The postural instability of the wearer is then in majority induced by motion in the anterior-posterior direction and its effect is minimized by setting the angle of the inclined portion to 180 degrees. In that case, the inset is set to zero.

Further, when said computed value is less than the second threshold, the angle of the inclined portion decreases as the computed value decreases. The angle of the inclined portion may decrease continuously or abruptly to reach the prescription angle value.

According to an embodiment, when said computed value is greater than a third threshold, the angle of the inclined portion continuously increases from a prescribed angle value to 180°. The inset thus decreases. As the wearer is more sensible to motion in the anterior-posterior direction, the angle departs from the prescribed angle value to improve the viewing comfort of the wearer.

Thus, when the computed value is lower than the third threshold, the third threshold being lower than the second threshold, the angle of the inclined portion corresponds to a prescription value R which may correspond to a standard value representative of a given population of wearers or to a value specific to the wearer corresponding to the binocular convergence when the wearer is seeing an object placed in the near-vision zone at a given distance. For example, a standard value of inset is of 2.5 mm, which, for a progression length of 17 mm, corresponds to an angle of 8 degrees approximately. In that case, the progression length corresponds to the length of the inclined portion. This value is given for illustration purposes only.

It may be noted that the length of the inclined portion does not necessarily correspond to the progression length and that the progression may vary in different ways along the meridian line, i.e. have different progression lengths, according to the type of progressive lens design used. However, the angle cc will remain unchanged and reflects the value of inset that will be used in the lens design.

According to an embodiment, the fourth threshold is lower than the third threshold V3 as represented in FIG. 6. In such an embodiment, only one of the angle of the inclined portion and the reparation is continuously varied while the other design parameter is constant.

Step S1220 further comprises a step S1224 of determining the design of the progressive lens, i.e. the surface characteristics of the progressive lens, taking into account the characteristics of the progressive lens set in step S1222 and the prescription of the future wearer. Different methods known of the person skilled in the art may be used.

According to an embodiment, the design of the progressive lens is obtained by running an optimization algorithm configured to maximize a merit function while taking into account different constraints and design parameters including the angle of the inclined portion of the meridian line and the first and second progression profiles.

The design parameters may further comprise a lens hardness parameter such as the one disclosed in WO 2009/

043941 page 8, lines 10-19 or a progression length determined as a function of a measurement of the global postural instability of the wearer. The global postural instability of the wearer is for example measured when the future wearer is seeing a visual pattern moving in random directions. The measurement of the global postural instability is to oppose to a measurement of the postural instability performed when the wearer is seeing a visual pattern moving in a mediolateral or an anterior-posterior direction.

According to another embodiment, the design of the progressive lens may be determined based on an existing "model design" in which at least the amount of progression on the front and back surface corresponds to the values set in step S1123. The inset may be modified using one of the methods described in WO2008/030102 for modifying the inset of a progressive lens having a given "model design" when one of the front or back surfaces has a fixed progression profile with a predetermined value of inset which corresponds to the prescription value R. The progressive lens is then manufactured using a semi-finished lens having a finished surface with a progression profile with an inset having the prescription value R. The other surface is re-machined to provide the prescription of the wearer and the wanted value of inset.

A progressive lens is then manufactured based on the surface characteristics of the progressive lens determined in step S1200.

Figure 7:
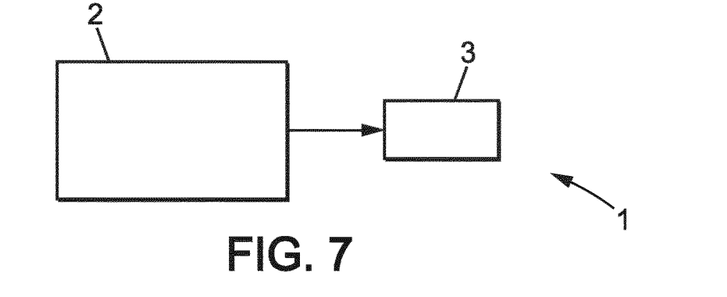
FIG. 7 represents a system for determining a design of a progressive lens according to one embodiment.

FIG. 7 represents a system for implementing one of the methods described in relation to FIGS. 2 and 5 according to an embodiment. The system 1 comprises a device 2 configured to display a visual pattern moving at least along at least a mediolateral direction and to measure the postural instability of the future wearer when the future wearer is seeing a visual pattern along at least a mediolateral direction. The device 2 may also be configured to display a visual pattern moving along the anterior-posterior direction and to measure the postural instability of the future wearer when the future wearer is seeing a visual pattern along the anterior-posterior direction.

The system also comprises a calculator 3 configured to obtain measurements of a postural instability of the future wearer when seeing a visual pattern moving at least along an anterior-posterior direction and to determine the design of the progressive lens according to the obtained measurements. The calculator may be for example a processor, a microprocessor, or a micro-controller.

In the embodiment described here, the device 2 transmits the measurements of the postural instability of the future wearer to the calculator 3. The calculator is then a processor comprised in a personal computer which comprises a memory in which instructions for implementing the method are stored.

According to another embodiment, the calculator 3 is comprised within the device 2 and is also configured to trigger the display of the visual pattern and to measure the postural instability of the wearer when the wearer is seeing the corresponding visual pattern.

As described above, the postural instability is computed based on measurements of changes in the body posture of the wearer. These changes in the body posture may be measured by detecting movements of the future wearer using a camera and optical targets or movement sensors or a force platform. The calculator is then configured to receive the measurements of changes in the body posture and to compute the postural instability based on those measurements.

The invention claimed is:

1. A method for determining a design of a progressive lens intended to be worn by a wearer, the progressive lens including a front surface and a back surface disposed closer to an eye of the wearer, the front surface including a first progression profile and the back surface including a second progression profile, the method comprising:
   measuring changes in a body posture of the wearer by sensing movements of the wearer when seeing a visual pattern moving along a mediolateral direction, where the mediolateral direction is with respect to the wearer and is in contrast to vertical and anteroposterior directions;
   obtaining first data representative of a first measurement of a first postural instability of the wearer when seeing the visual pattern moving along the mediolateral direction, the first measurement being determined by the measuring changes in the body posture of the wearer when seeing the visual pattern moving along the mediolateral direction, the mediolateral direction corresponding to a horizontal direction in a plane parallel to a frontal plane, which is perpendicular to a median plane;
   determining, by at least one processor, a repartition between the first progression profile and the second progression profile based on the first data, wherein, when said repartition is defined by a progression profile on the back surface versus a complementary progression profile on the front surface, said repartition is an increasing function of said first postural instability; and
   determining surface characteristics of the progressive lens to be manufactured based on the repartition determined between the first progression profile and the second progression profile.

2. The method of claim 1, wherein said first and second progression profiles defining a meridian line extending from a distance-vision point to a near-vision point, said meridian line including a vertical portion passing through the distance-vision point and an inclined portion passing through the near-vision point, the vertical portion and the inclined portion forming an angle between them, the method further comprising:
   obtaining second data representative of a second measurement of a second postural instability of the wearer when seeing a visual pattern moving along an anterior-posterior direction; and
   determining, by said at least one processor, the angle of the inclined portion based on said second data.

3. The method of claim 2, further comprising:
   obtaining a comparison value representing a comparison between the first measurement and the second measurement, said comparison value being increased when the first measurement increases while the second measurement decreases, and being decreased when the first measurement decreases while the second measurement increases;
   when said comparison value is lower than a first threshold, then the second progression profile is set to correspond to the full progression profile of the lens, while the first progression profile is set to be null, and when said comparison value is greater than the first threshold, the first progression profile is set to increase as the comparison value increases while the second progression profile decreases; and
   when said comparison value is greater than a second threshold, the angle of the inclined portion is equal to 180°, while when said comparison value is less than the second threshold, the angle of the inclined portion decreases as the comparison value decreases, the second threshold being greater than the first threshold.

4. The method according to claim 3, wherein when said comparison value is greater than a third threshold lower than said second threshold, the angle of the inclined portion continuously increases from a prescribed angle value to 180°.

5. The method according to claim 4, wherein when said comparison value is between said first threshold and a fourth threshold greater than said first threshold, the second progression profile continuously decreases from the first threshold to reach a null progression profile at said fourth threshold, while the first progression profile continuously increases to reach the full progression profile at said fourth threshold.

6. The method according to claim 5,
wherein the fourth threshold is lower than the third threshold, and
wherein when said comparison value is between said first threshold and a fourth threshold greater than said first threshold, the second progression profile continuously decreases from the first threshold to reach a null progression profile at said fourth threshold, while the first progression profile continuously increases to reach the full progression profile at said fourth threshold.

7. A system for determining a design of a progressive lens intended to be worn by a wearer, the progressive lens comprising a front surface and a back surface disposed closer to an eye of the wearer, the front surface comprising a first progression profile and the back surface comprising a second progression profile, the system comprising:
measurement circuitry configured to measure changes in a body posture of the wearer by sensing movements of the wearer when seeing a visual pattern moving along a mediolateral direction, where the mediolateral direction is with respect to the wearer and is in contrast to vertical and anteroposterior directions;
at least one processor configured to:
obtain first data representative of a first measurement of a first postural instability of the wearer when seeing the visual pattern moving along the mediolateral direction, the first measurement being determined by the measuring changes in the body posture of the wearer when seeing the visual pattern moving along the mediolateral direction, the mediolateral direction corresponding to a horizontal direction in a plane parallel to a frontal plane which is perpendicular to a median plane,
determine a repartition between the first progression profile and the second progression profile based on said first data, wherein, when said repartition is defined by a progression profile on the back surface versus a complementary progression profile on the front surface, said repartition is an increasing function of said first postural instability, and
determine surface characteristics of the progressive lens to be manufactured based on the repartition determined between the first progression profile and the second progression profile.

8. The system of claim 7, wherein said first and second progression profiles define a meridian line extending from a distance-vision point to a near-vision point, said meridian line comprising a vertical portion passing through the distance-vision point and an inclined portion passing through the near-vision point, the vertical portion and the inclined portion forming an angle between them, said at least one processor being further configured to:

obtain second data representative of a second measurement of a second postural instability of the wearer when seeing a visual pattern moving along an anterior-posterior direction, and
determine the angle of the inclined portion based on said second data.

9. The system of claim 8, wherein said at least one processor is further configured to:
obtain a comparison value representing a comparison between the first measurement and the second measurement, said comparison value being increased when the first measurement increases while the second measurement decreases, and being decreased when the first measurement decreases while the second measurement increases,
when said comparison value is lower than a first threshold, then set the second progression profile to correspond to the full progression profile of the lens, while the first progression profile is set to be null, and when said comparison value is greater than the first threshold, set the first progression profile to increase as the comparison value increases while the second progression profile decreases, and
wherein when said comparison value is greater than a second threshold, the angle of the inclined portion is equal to 180°, while when said comparison value is less than the second threshold, the angle of the inclined portion decreases as the comparison value decreases, the second threshold being greater than the first threshold.

10. The system of claim 7, wherein the system further comprises:
a display device configured to display a visual pattern moving at least along at least an anterior-posterior direction, and
a device configured to measure the postural instability of the wearer when the wearer is seeing the visual pattern along at least an anterior-posterior direction.

11. A non-transitory computer-readable storage medium, storing a computer program that when executed by a computer causes the computer to implement the method according to claim 1.

12. The method according to claim 4, wherein when said comparison value is between said first threshold and a fourth threshold greater than said first threshold, the second progression profile continuously decreases from the first threshold to reach a null progression profile at said fourth threshold, while the first progression profile continuously increases to reach the full progression profile at said fourth threshold.

13. The system of claim 8, wherein the system further comprises:
a display device configured to display a visual pattern moving at least along at least an anterior-posterior direction, and
a device configured to measure the postural instability of the wearer when the wearer is seeing the visual pattern along at least an anterior-posterior direction.

14. The system of claim 9, wherein the system further comprises:
a display device configured to display a visual pattern moving at least along at least an anterior-posterior direction, and
a device configured to measure the postural instability of the wearer when the wearer is seeing the visual pattern along at least an anterior-posterior direction.

15. A method for generating a design of a progressive lens intended to be worn by a wearer, the progressive lens including a front surface and a back surface disposed closer to an eye of the wearer, the front surface including a first progression profile and the back surface including a second progression profile, the method comprising:

measuring changes in a body posture of the wearer by sensing movements of the wearer when seeing a visual pattern moving along a mediolateral direction, where the mediolateral direction is with respect to the wearer and is in contrast to vertical and anteroposterior directions;

first measuring of a first postural instability of the wearer when seeing the visual pattern moving along the mediolateral direction, the first measuring being determined by the measuring changes in the body posture of the wearer when seeing the visual pattern moving along the mediolateral direction, the mediolateral direction corresponding to a horizontal direction in a plane parallel to a frontal plane, which is perpendicular to a median plane;

obtaining first data representative of the first measurement of the first postural instability of the wearer when seeing the visual pattern moving along the mediolateral direction;

determining, by a processor, a repartition between the first progression profile and the second progression profile based on the first data, wherein, when said repartition is defined by a progression profile on the back surface versus a complementary progression profile on the front surface, said repartition is an increasing function of said first postural instability;

determining, by the processor, surface characteristics of the progressive lens to be manufactured based on the repartition determined between the first progression profile and the second progression profile; and     generating, by the processor, the design of the progressive lens to be manufactured based on the determined surface characteristics.

16. The method of claim 1, further comprising: manufacturing the progressive lens based on the determined surface characteristics of the progressive lens.

\* \* \* \* \*